(12) United States Patent
Jacques

(10) Patent No.: US 6,357,437 B1
(45) Date of Patent: Mar. 19, 2002

(54) WASTE GAS RECOVERY APPARATUS

(75) Inventor: Norman Jacques, Churchill (CA)

(73) Assignee: Vortex Recoveries Inc., Mississauga (CA)

( * ) Notice: Subject to any disclaimer, the term of this patent is extended or adjusted under 35 U.S.C. 154(b) by 0 days.

(21) Appl. No.: 09/502,438

(22) Filed: Feb. 11, 2000

(30) Foreign Application Priority Data

Feb. 19, 1999 (CA) .............................................. 2262393

(51) Int. Cl.[7] .............................................. A62B 19/00
(52) U.S. Cl. .......................... 128/201.25; 128/205.25; 128/206.21
(58) Field of Search ................... 128/200.24, 203.12, 128/204.18, 205.25, 205.27, 206.12, 206.21, 201.25

(56) References Cited

U.S. PATENT DOCUMENTS

| | | |
|---|---|---|
| 5,474,060 A | 12/1995 | Evans |
| 5,676,133 A | 10/1997 | Hickle et al. |
| 5,899,832 A * | 5/1999 | Hougen ........................ 482/13 |
| 6,145,503 A * | 11/2000 | Smith ..................... 128/202.16 |

FOREIGN PATENT DOCUMENTS

CA          1259872          9/1989

* cited by examiner

Primary Examiner—Glenn K. Dawson
(74) Attorney, Agent, or Firm—Arne I. Fors

(57) ABSTRACT

A post-operative anaesthesia recovery apparatus that permits anaesthetic waste gases exhaled by a patient to be withdrawn and discharged outside the unit. The apparatus includes a face mask having a recovery port and an oxygen port. The oxygen port allows oxygen to be fed to the patient. The recovery port is attached to a suction evacuation assembly, which is in turn attached to a discharge assembly. An air entrainment cartridge attaches the evacuation assembly to the recovery port. The cartridge is provided with longitudinal channels that allow a flow of air into the apparatus. The entrained air maintains a slightly sub-atmospheric pressure within the apparatus and allows the patient to breathe normally without complex valve systems.

11 Claims, 3 Drawing Sheets

WASTE GAS RECOVERY APPARATUS

FIELD OF THE INVENTION

The present invention relates to health care, or patient care, equipment. In particular, the present invention relates to an apparatus for recovering waste gas from a patient's exhalations in a post-anaesthesia care unit.

BACKGROUND OF THE INVENTION

Anaesthetic gases are commonly given to patients undergoing surgery. As is well known, overexposure to anaesthetic and analgesic gases, such as nitrous oxide, halothane, enflurane, isoflurane, desflurane and sevoflurane, poses serious health risks to health care workers. Both short term and long term exposure to anaesthetic gases can adversely affect performance, cognition, audiovisual ability and dexterity among health care workers. To mitigate the recognized health risks to medical personnel, recommended exposure limits have been established by government agencies, such as the U.S. Department of Health and Human Services.

The anaesthetics gases are typically administered to an intubated patient through the use of a tracheal tube that is attached to a closed scavenging circuit. The patient inhales an anaesthetic gas mixture, and exhales residual unmetabolized anaesthetic gases. Nitrous oxide ($N_2O$), which is commonly used as a carrier for other anaesthetic gases, is the most prevalent compound in the exhaled gases because it is not metabolized in the body and is excreted with each exhalation by the patient. In the closed anaesthetic system used in an operating room, the scavenging circuit limits the exposure of surgical staff. However, once the surgery is completed, the patient is extubated and left to recover in a post anaesthesia care unit. In the post anaesthesia care unit, the patient continues to expel anaesthetic gases, or "off-gas" for a period of time, generally 20–30 minutes. As a result, if several patients are recovering in a post anaesthesia care unit, the level of nitrous oxide and other anaesthetic gases can quickly exceed the recommended time averaged exposure limit, currently 25 parts per million (ppm) in the United States.

To deal with this problem, hospitals and other surgical centers require an efficient and cost effective method of handling the contamination of post anaesthesia care units that reduces the risk to medical workers without risking patient health.

Canadian Patent No. 1,259,872 to Lindkvist discloses a gas collecting device in the form of a double-walled, hollow, cup-shaped mask that fits around a patient's chin. The device is attached to a suction system which draws away a portion of the patient's exhalations. This device is intended for the administration of anaesthesia in a dental office, where it is necessary for the dentist to work in the mouth cavity. Since it does not cover the patient's nose and mouth, a large portion of the anaesthetic gases are still expelled directly into the atmosphere. Further, the device is large, bulky and semi-rigid material which could possibly injure an unconscious patient.

U.S. Pat. No. 5,474,060 to Evans discloses a face mask for administering a gas to a patient and monitoring the patient's exhalations for oxygen and carbon dioxide levels. By and large, the air exhaled by the patient is exhausted through conventional side vents. However, a portion of the exhaled air is diverted and sampled through a tube attached to a sampling unit. This device permits the controlled administration of oxygen, which is often required by patients post-anaesthesia, but does not address the problem of recovering anaesthetic gases off-gassed by the patient.

U.S. Pat. No. 5,676,133 to Hickle et al. discloses a post-operative anaesthesia recovery system. The system includes a face mask that is attached to an oxygen supply and a scavenging unit. The system is closed, and is intended to recover all the air exhaled by the patient, and is essentially a post-operative version of the scavenging system used in an operating room. Because this system is fully sealed, it requires a number of specialized adapters and valves to permit the patient to inhale and exhale without undue effort. The patient's breathing must also be constantly monitored to ensure that breathing remains normal. As a result, this system is not cost effective in most post-anaesthesia units.

It is therefore desirable to provide an apparatus for removing anaesthesia gases exhaled by a patient in a post-anaesthesia care unit that overcomes the limitations of the prior art. In particular, it is desirable that such an apparatus maintain the level of anaesthetic gases in a post-anaesthesia care unit to within suggested limits, permit a patient to be administered oxygen, allow normal breathing by the patient. The apparatus should also be relatively inexpensive, and simple to install in existing post-operative anaesthesia units.

SUMMARY OF THE INVENTION

In a first embodiment according to the present invention, there is provided a post-operative gas recovery apparatus, comprising:

a mask for sealingly engaging a patient's face to capture waste anaesthetic gases exhaled by a patient, the mask including a recovery port in fluid communication with an evacuation assembly for drawing the waste anaesthetic gases to a discharge assembly, and an oxygen port for communicating with an oxygen source for providing oxygen to the patient;

an air entrainment cartridge interconnecting the evacuation assembly and the recovery port to permit fluid communication therebetween, the air entrainment cartridge including entrainment means permitting a flow of atmospheric air to enter the apparatus to provide a pressure inside the mask that allows the patient to breathe in a conventional manner.

In a further embodiment according to the present invention there is provided an air entrainment cartridge for a post-operative gas recovery apparatus, comprising:

a hollow tube having a distal end for attaching to a recovery port of a mask; a proximal end for attaching to an evacuation assembly; and air entrainment means for permitting a flow of atmospheric air to be entrained within the tube.

In a preferred embodiment of the present invention, the air entrainment means are channels formed on the outside of the air entrainment cartridge. The channels are incised longitudinally into the cartridge, and are only partially covered by tubing leading to a blower unit.

BRIEF DESCRIPTION OF THE DRAWINGS

Preferred embodiments of the present invention will now be described, by way example only, with reference to the attached Figures, in which.

DETAILED DESCRIPTION

Figure 1:
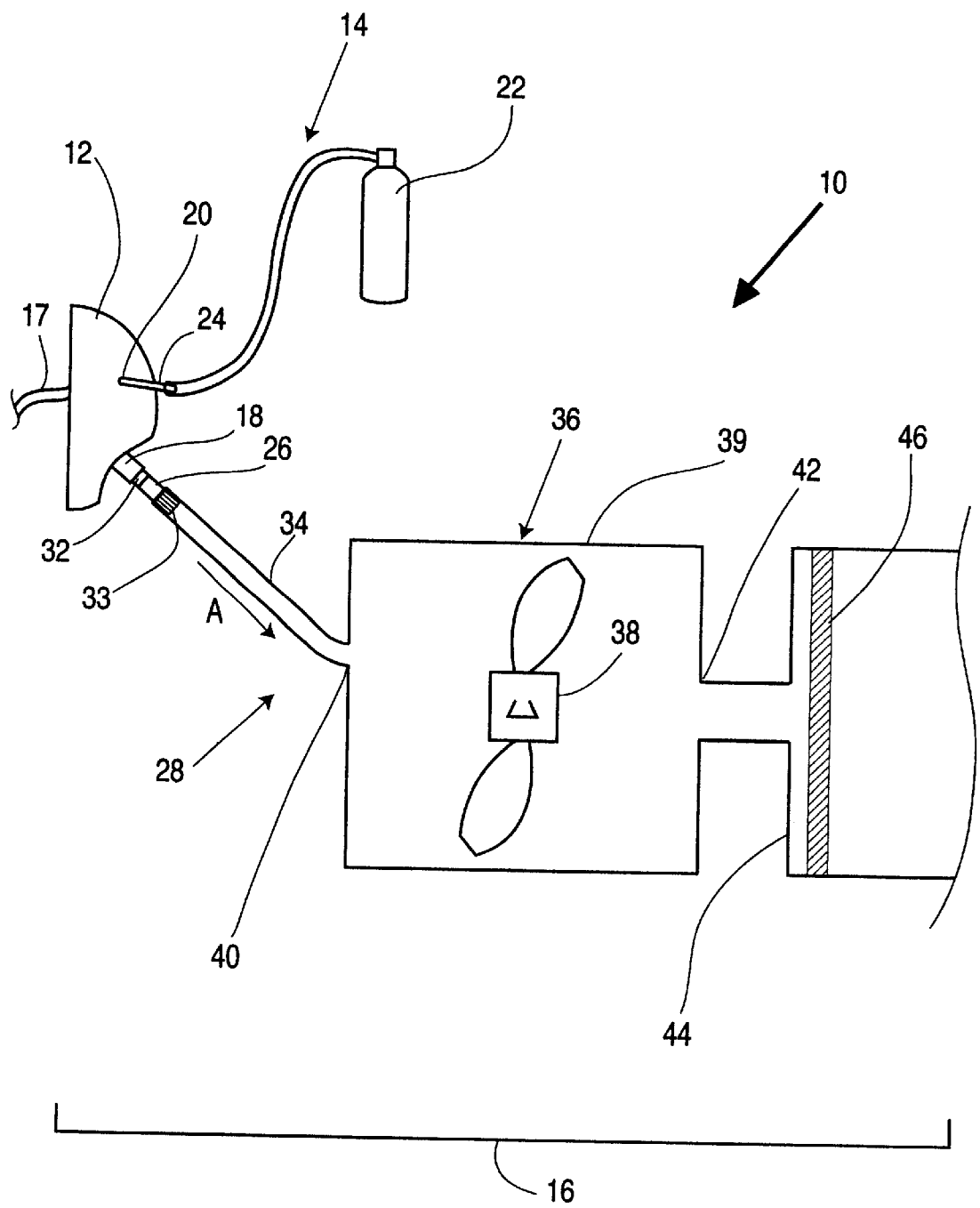
FIG. 1 shows a schematic view of a post-operative recovery apparatus according to an embodiment of the present invention.

FIG. 1 shows a post-operative recovery apparatus according to an embodiment of the present invention (not to scale), and generally designated as 10. Apparatus 10 generally consists of a mask 12, a conventional oxygen source 14, and a recovery system 16. Mask 12 is of a conventional shape defining a cavity that fits over, and forms a seal around, a patient's nose and mouth. An elastic strap 17 attached to either side of mask 12 permits it to be secured to a patient's head. Preferably, mask 12 is a pliable, molded, transparent rubber or plastic, such as polyvinyl chloride, polyethylene, polypropylene, polyurethane, or other suitable material. Mask 12 has two ports: a recovery port 18 and an oxygen port 20.

Oxygen source 14 is attached to mask 12 via oxygen port 20 and permits oxygen, or other suitable gas mix, to be administered to the recovering patient. In a preferred embodiment, oxygen source 14 consists of an oxygen tank 22 relaying oxygen to the patient through a tube, conventionally 1/8" tubing, that fits over a nipple 24 formed in mask 12 at oxygen port 20. For a typical adult patient, the oxygen is provided at a rate of approximately 6–8 liters per minute.

Recovery system 16 consists of an evacuation assembly 28 and a discharge assembly 30. An air entrainment cartridge 26 connects evacuation assembly 28 to mask 12. Air entrainment cartridge 26 is connected at its distal end 32 to recovery port 18, and at its proximal end 33 to a length of tube 34. In a preferred embodiment, tube 34 is conventional 19 mm inner diameter, flexible plastic tubing, and proximal end 33 has an appropriate outer diameter to permit tube 34 to be slid on and frictionally retained. Distal end 32 is similarly sized and attached to recovery port 18.

Evacuation assembly 28 consists of tube 34 and a blower unit 36 that draws air through tube 34 in the direction of the arrow marked "A" at a rate of approximately 4 liters per minute. In a preferred embodiment, blower unit 36 consists of an electric fan 38 within a housing 39 that has an inlet 40 and an outlet 42. Inlet 40 is attached, to tube 34, while outlet 42 communicates with discharge assembly 30. Blower unit 36 is provided with pressure sensors to monitor the pressure at which the air is withdrawn through evacuation assembly 28, and is electrically controlled to maintain flow at the rates detailed above.

Discharge assembly 30 consists of a backing plate 44 which is attached to an exhaust grill 46. Plate 44 is attached, either directly as shown, or through another length of tubing, to evacuation assembly 28. Exhaust grill 46 will typically lead to a hospital's exhaust conduits, and thence to the exterior of the building to permit the withdrawn gases to be exhausted to the atmosphere outside the post-anaesthesia care unit. It is fully within the contemplation of the inventor that discharge assembly 30 can exhaust into a containment facility or scavenging unit, rather than directly to the atmosphere, if desired.

Figure 2:
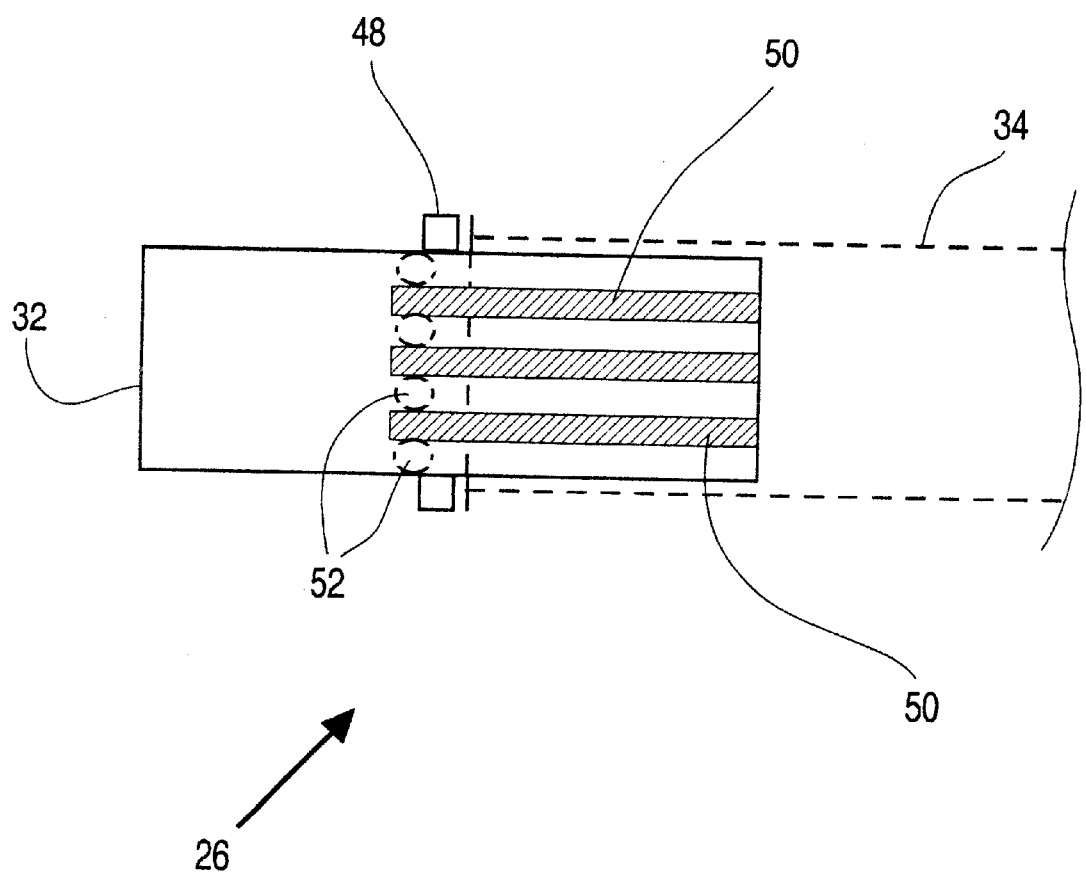
FIG. 2 shows an air entrainment cartridge according to an embodiment of the present invention.
Figure 3:
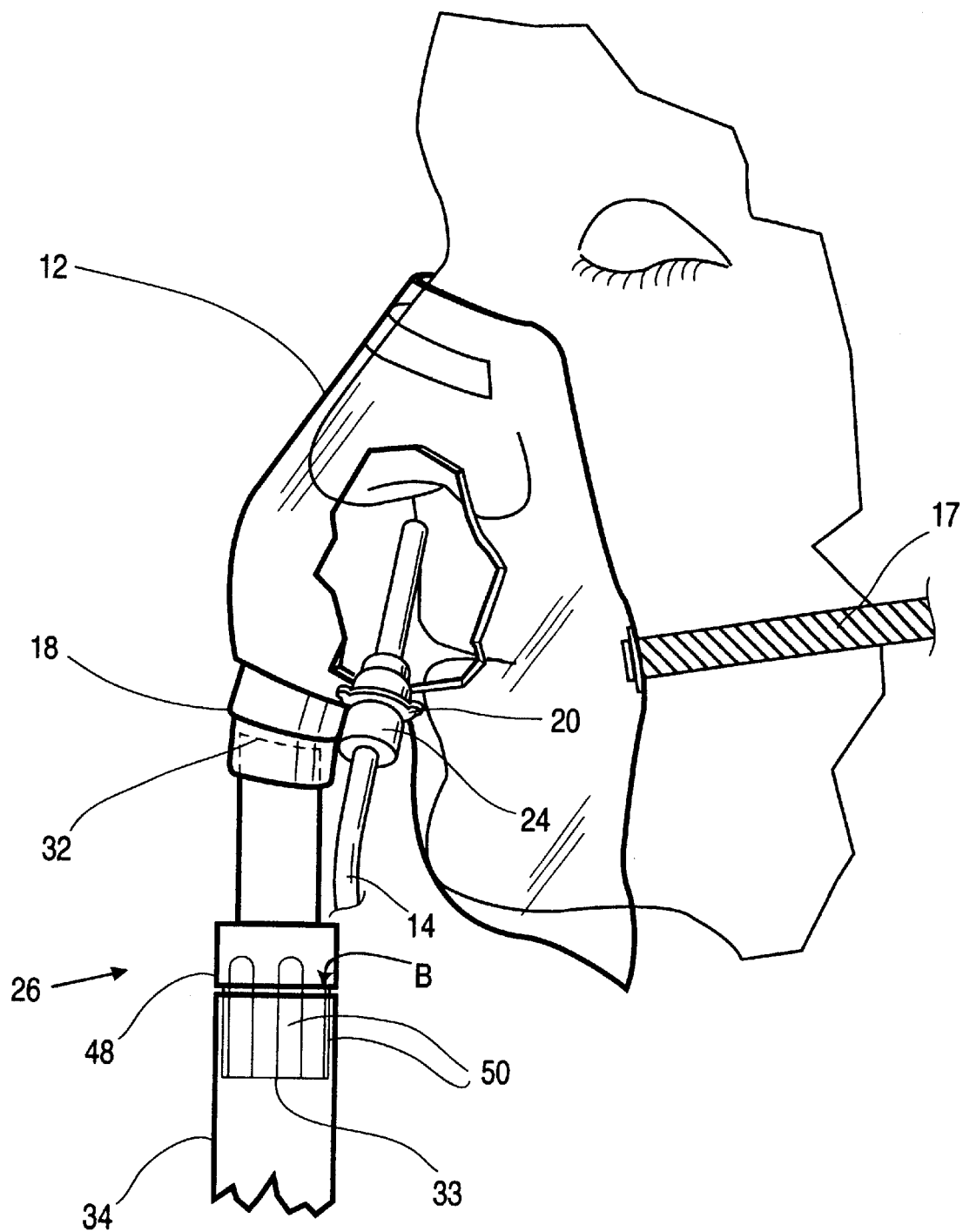
FIG. 3 shows a perspective view of the mask portion of the post-operative recovery apparatus of FIG. 1.

Referring to FIG. 2, a preferred embodiment of air entrainment cartridge 26 is shown in greater detail. Air entrainment cartridge 26 is a rigid, hollow tube having an outer diameter of approximately 19 mm, and an inner diameter of approximately 16 mm. At approximately the midpoint between proximal end 33 and distal end 32 there is a stop 48 formed circumferentially around the exterior surface of air entrainment cartridge 26. A number of longitudinal channels 50 are formed in the exterior surface and extend from proximal end 33 to a point beyond stop 50 such that when tube 34 (shown in dotted lines) is attached and abuts stop 48, channels 50 remain partially exposed. Channels 50 have a depth of approximately 2 mm. The purpose of channels 50 is to permit a thin stream of atmospheric air from the post-anaesthesia care unit to be drawn into apparatus 10 to maintain a slightly sub-atmospheric pressure within mask 12 that allows a patient to breathe normally. Channels 50 can be replaced by apertures 52(shown in ghost lines) piercing air entrainment cartridge 26, or any other means that allows atmospheric air to enter apparatus 10. Air entrainment cartridge 26 can be made of any hard molded plastic or metal material. FIG. 3 shows the attachment of air entrainment cartridge 26 to mask 12 and tube 34 in greater detail.

The operation of apparatus 10 will now be described with reference to FIGS. 1–3. After surgery, anaesthetised patients are extubated and placed in a recovery room. Mask 12 is placed over the recovering patient's nose and mouth such that it seals at its edges, and is secured in place by strap 17. Typically, the mask will remain over the patient's face for 20–30 minutes. Oxygen is fed to the patient through oxygen port 20. As the patient exhales, the waste anaesthetic gases are drawn through air entrainment cartridge 26, and into tube 34 by blower unit 36. The waste gases are then exhausted through exhaust grill 46.

As the waste gases are being withdrawn, a stream of air, from within the post-anaesthesia care unit, is entrained into apparatus 10 through the exposed ends of channels 50, as shown by arrow "B" in FIG. 3. This entrainment of air through channels 50 causes the pressure within mask 12 to be only slightly less than the ambient atmospheric pressure within the post-anaesthesia care unit, and permits the patient to breathe in a normal manner without requiring elaborate valves and control systems. Typically, the rate at which the waste gases are withdrawn is controlled such that the sub-atmospheric pressures, as sensed at blower unit 36, do not exceed 35–38 mm Hg.

While channels 50 also allow some waste anaesthetic gases to "leak" into the post-anaesthesia care unit, it has been found that approximately 95%–98% of the waste anaesthetic gases are recovered and exhausted through exhaust grill 46. A 2%–5% level of leakage does not result in waste gases reaching a level in excess of recommended limits within the post-anaesthesia care unit.

To those of skill in the art, the advantages of the present invention over prior art waste gas recovery systems will be apparent. The present post-operative gas recovery apparatus 10 is easily installed, connects directly to existing exhaust ducting, and keeps harmful waste anaesthetic gases to within acceptble limits in a post-anaesthesia care unit. The air entrainment cartridge means that elaborate valves and control systems are not required to permit a patient to breathe in a normal manner, nor is extensive or specialized patient monitoring required. Oxygen can also be administered to the patient as he is recovering.

The above-described embodiments of the invention are intended to be examples of the present invention and alterations and modifications may be effected thereto, by those of skill in the art, without departing from the scope of the invention which is defined solely by the claims appended hereto.

I claim:
1. A post-operative gas recovery apparatus, comprising:
a mask for sealingly engaging a patient's face to capture waste anaesthetic gases exhaled by a patient, the mask including a recovery port in fluid communication with an evacuation assembly for drawing the waste anaesthetic gases to a discharge assembly, and an oxygen port for communicating with an oxygen source for providing oxygen to the patient;
an air entrainment cartridge interconnecting the evacuation assembly and the recovery port to permit fluid communication therebetween, the air entrainment cartridge including entrainment means permitting a flow of atmospheric air to enter the apparatus to provide a pressure inside the mask that allows the patient to breathe in a conventional manner.

2. A post-operative gas recovery apparatus according to claim 1, wherein the anaesthetic gases include nitrous oxide.

3. A post-operative gas recovery apparatus according to claim 1, wherein the evacuation assembly includes a blower unit for withdrawing the gases at a controlled rate of flow.

4. A post-operative gas recovery apparatus according to claim 3, wherein the rate is in the range of approximately 4 liter per minute.

5. A post-operative gas recovery apparatus according to claim 1, wherein the entrainment means include channels formed on an exterior surface of the air entrainment cartridge.

6. A post-operative gas recovery apparatus according to claim 1, wherein the entrainment means include apertures communicating between an interior and an exterior of the air entrainment cartridge.

7. A post-operative gas recovery apparatus according to claim 1, wherein the pressure is in the range of approximately 35 to 38 mm Hg.

8. A post-operative gas recovery apparatus according to claim 1, wherein the air entrainment cartridge comprises a hollow tube having a distal end for attaching to the recovery port of the mask; a proximal end for attaching to the evacuation assembly; and air entrainment means formed in the tube for permitting a flow of atmospheric air to be entrained within the tube.

9. A post-operative gas recovery apparatus according to claim 8, wherein the hollow tube has a stop between the distal and proximal ends, the stop preventing blockage of the air entrainment means by evacuation tubing.

10. A post-operative gas recovery apparatus according to claim 9, wherein the entrainment means include channels formed on an exterior surface of the tube.

11. A post-operative gas recovery apparatus according to claim 9, wherein the entrainment means include apertures formed in the tube communicating between an interior and an exterior of the tube.

* * * * *